United States Patent
Qaysi

(10) Patent No.: US 9,931,277 B2
(45) Date of Patent: Apr. 3, 2018

(54) DRUG AND FLUID DISPENSER

(71) Applicant: Zahra Miswak Qaysi, Kent, OH (US)

(72) Inventor: Zahra Miswak Qaysi, Kent, OH (US)

( * ) Notice: Subject to any disclaimer, the term of this patent is extended or adjusted under 35 U.S.C. 154(b) by 341 days.

(21) Appl. No.: 14/737,226

(22) Filed: Jun. 11, 2015

(65) Prior Publication Data

US 2016/0361524 A1 Dec. 15, 2016

(51) Int. Cl.
*A61J 7/00* (2006.01)
*A61J 3/00* (2006.01)
*A61M 31/00* (2006.01)

(52) U.S. Cl.
CPC .............. *A61J 3/002* (2013.01); *A61J 7/0007* (2013.01); *A61M 31/00* (2013.01)

(58) Field of Classification Search
CPC A61J 7/0084; A61J 7/04; A61J 7/0409; A61J 7/0427; A61J 7/0436; A61J 7/0445; A61J 7/0454; A61J 7/0472; A61J 7/0481
See application file for complete search history.

(56) References Cited

U.S. PATENT DOCUMENTS 3,712,507 A * 1/1973 Holt .................. G07F 11/54
221/150 R
3,998,356 A * 12/1976 Christensen .......... A61J 7/0481
221/2
4,087,020 A * 5/1978 Krakauer ................ G07F 11/52
221/155
4,409,695 A 10/1983 Johnston et al.
4,573,606 A * 3/1986 Lewis ................... A61J 7/0481
221/15
4,616,752 A * 10/1986 Ridgley .................... A61J 1/03
206/521

(Continued)

FOREIGN PATENT DOCUMENTS

CN 102885679 A 1/2013
EP 0 533 300 A1 3/1993

(Continued)

OTHER PUBLICATIONS

"Ivation Automatic Pill Dispenser" http://www.homecontrols.com/s.nl?search=Ivation+Automatic+Pill+Dispenser+GMI.

(Continued)

*Primary Examiner* — Kami A Bosworth
*Assistant Examiner* — William Carpenter
(74) *Attorney, Agent, or Firm* — Oblon, McClelland, Maier & Neustadt, L.L.P.

(57) ABSTRACT

A drug and fluid dispenser includes a first mechanism for holding and dispensing a fluidized food; a second mechanism for measuring, holding, and dispensing a specified amount of fluid to be taken with a set of medicines at a specified time; a third mechanism for holding and dispensing one or more sets of medicines in a chronological order according to a pre-determined schedule of administration to an individual; a fourth mechanism for granulating a next scheduled set of medicines and mixing the granulated next scheduled set of medicines with the specified amount of fluid at the specified time; a first output mechanism for administering contents of the first mechanism and contents of the fourth mechanism to the individual; and a second output mechanism for rinsing the fourth mechanism subsequent to administration of each of the sets of medicines.

7 Claims, 7 Drawing Sheets

(56) References Cited

U.S. PATENT DOCUMENTS

| | | | | |
|---|---|---|---|---|
| 4,747,514 | A * | 5/1988 | Stone | A61J 7/0481 |
| | | | | 221/15 |
| 4,911,327 | A * | 3/1990 | Shepherd | A61J 7/0481 |
| | | | | 221/15 |
| 7,543,766 | B2 | 6/2009 | Dobson | |
| 7,670,479 | B2 | 3/2010 | Arett et al. | |
| 8,145,353 | B1 | 3/2012 | Cotner | |
| 2002/0074339 | A1 | 6/2002 | Gilmore | |
| 2007/0029213 | A1* | 2/2007 | Hall | A61J 7/0084 |
| | | | | 206/217 |
| 2014/0244033 | A1* | 8/2014 | Ucer | A61J 7/0481 |
| | | | | 700/237 |
| 2016/0287477 | A1* | 10/2016 | Katz | A61J 7/0076 |

FOREIGN PATENT DOCUMENTS

| | | |
|---|---|---|
| JP | 2012-115634 A | 6/2012 |
| KR | 10-1007951 B1 | 1/2011 |

OTHER PUBLICATIONS

"Freedom Bed—Automatic Lateral Rotation" http://www.broadenedhorizons.com/freedom-bed.

"Philips Medido Pill Dispenser Simplifies Patient Adherence to Drug Regimens" Feb. 21, 2014 http://www.medgadget.com/2014/02/medido-automatic-pill-dispenser-from-philips-simplifies-patient-adherence-to-drug-regimens.html.

* cited by examiner

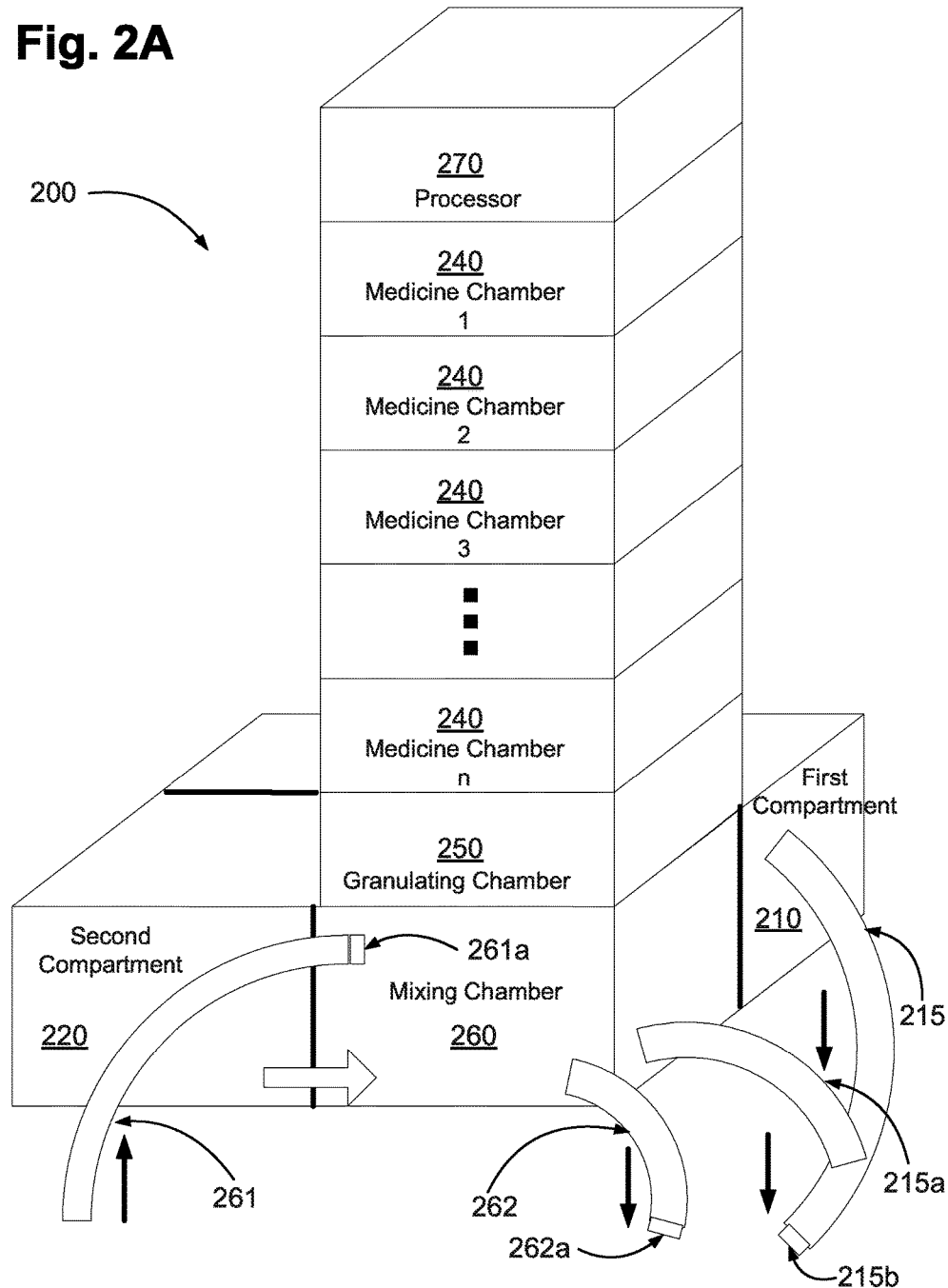

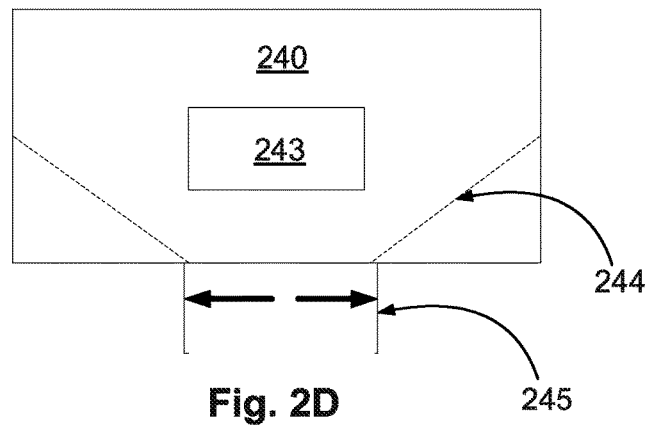
Fig. 2D
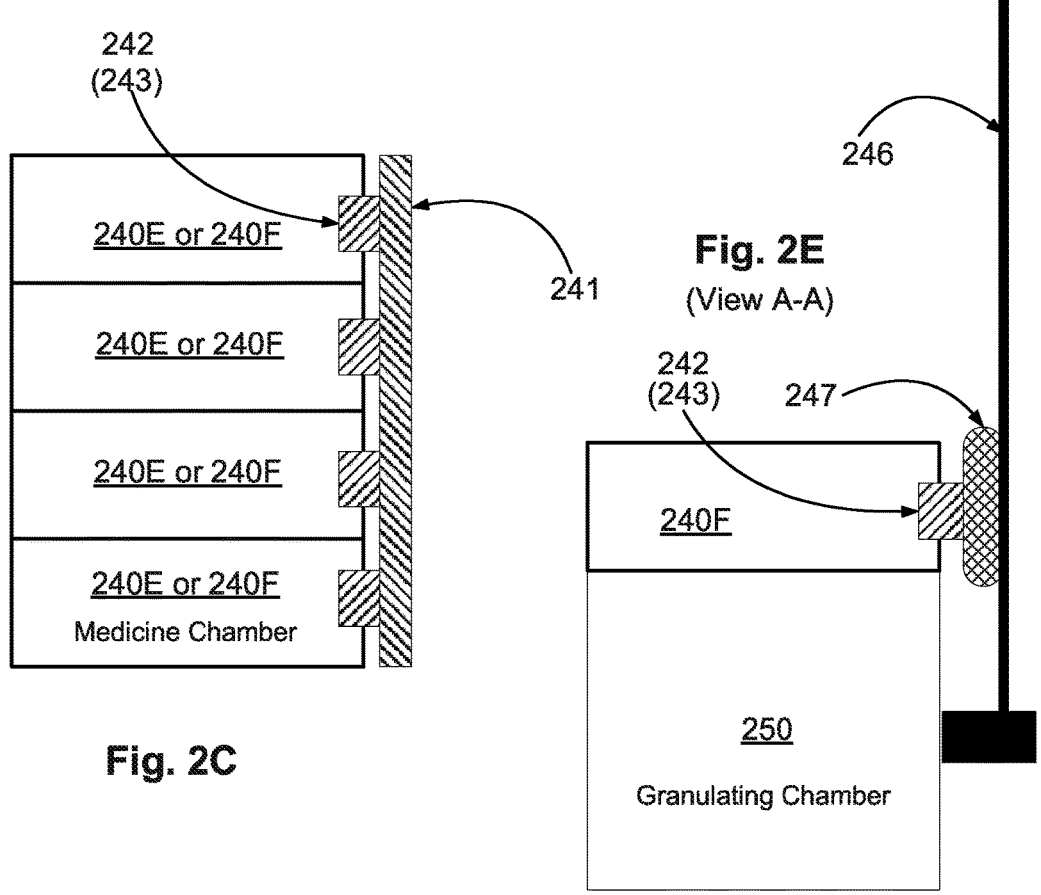
Fig. 2C
Fig. 2E
(View A-A)

DRUG AND FLUID DISPENSER

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In certain instances, an individual may be incapable of feeding himself/herself and may also be incapable of taking medication, especially medication in pill form. Such individuals may be partially or completely incapacitated due to injury or illness, such as a tracheotomy, a gastrointestinal disease, or malnourishment. Other individuals may be elderly and not have complete muscular and motor control, such as the ability to swallow whole foods and medications in pill form.

Certain devices attempt to compensate for temporary and permanent disabilities in swallowing whole foods and medications in pill form. The food can be liquefied and fed to an individual by an inserted feeding tube. This eliminates the need to swallow the food and also directs the food past an inserted endotracheal tube and directly into the stomach.

Pill medications can be added to the liquefied food which eliminates the need for an individual to swallow a hard solid pill. However, the pill medications tend to block a feeding tube, especially larger-sized pills. This requires removing the feeding tube to remove the blocked pill.

SUMMARY

In one embodiment, a drug and fluid dispenser includes a first compartment configured to hold a fluidized food, and a second compartment configured to hold a measured amount of fluid to be taken with a medicine. The drug and fluid dispenser also includes a third compartment configured as a medicine dispenser and granulator. The third compartment includes a plurality of medicine chambers, wherein each medicine chamber is configured to hold one or more medicines to be taken at a specified time. A lower medicine chamber holds one or more medicines to be taken at a first specified time, and each subsequently higher-positioned medicine chamber holds one or more medicines to be taken at respective subsequent times. The third compartment also includes a granulating chamber configured to grind, chop, or crush the one or more medicines into a powder. The third compartment also includes a processor including circuitry configured to drop the one or more medicines from the lower medicine chamber at the first specified time into the granulating chamber. The circuitry is also configured to lower the one or more medicines from each of the subsequently higher-positioned medicine chambers into a next lower medicine chamber for future dispensing. The third compartment also includes a mixing chamber configured to combine and mix the powder with the measured amount of fluid. The drug and fluid dispenser also includes a feeding mechanism configured to transport the combined powder and measured amount of fluid from the mixing chamber and to transport the fluidized food from the first compartment to an individual.

In another embodiment, a drug and fluid dispenser includes a fluidized food chamber configured to hold and dispense fluidized food to an individual. It also includes a fluid container configured to hold and dispense a measured amount of fluid with a scheduled medication dispensing. The drug and fluid dispenser also includes a plurality of medicine chambers. Each medicine chamber is configured to hold one or more medicines to be taken at a scheduled time. A lower medicine chamber holds one or more medicines to be taken at a first scheduled time, and each subsequently higher-positioned medicine chamber holds one or more medicines to be taken at their respective subsequently scheduled times. The drug and fluid dispenser also includes a mounted rail configured to connect with the plurality of medicine chambers and to forward rotate the plurality of medicine chambers at a next scheduled medication dispensing. A granulating chamber is configured to grind, chop, or crush the one or more medicines into a powder. A mixing chamber is configured to combine and mix the powder with the measured amount of fluid. A feeding mechanism is configured to transport the combined powder and measured amount of fluid from the mixing chamber and to transport the fluidized food from the fluidized food chamber to the individual. The drug and fluid dispenser also includes a processor circuit configured to open one or more doors on a bottom surface of the medicine chamber located directly above the granulating chamber, which causes the one or more medicines within the medicine chamber to be released into the granulating chamber at the next scheduled medication dispensing.

In another embodiment, a drug and fluid dispenser includes a first means for holding and dispensing a fluidized food, and a second means for measuring, holding, and dispensing a specified amount of fluid to be taken with a set of medicines at a specified time. The drug and fluid dispenser also includes a third means for holding and dispensing one or more sets of medicines in a chronological order according to a pre-determined schedule of administration to an individual. The drug and fluid dispenser also includes a fourth means for granulating a next scheduled set of medicines and mixing the granulated next scheduled set of medicines with the specified amount of fluid at the specified time. The drug and fluid dispenser also includes a first output means for administering contents of the first means and contents of the fourth means to the individual, and a second output means for rinsing the fourth means subsequent to administration of each of the sets of medicines.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2A is a block diagram illustrating a drug and food dispenser having a stationary rack according to one embodiment;

FIGS. 2B-2E are block diagrams illustrating a drug and food dispenser having a moving rail according to one embodiment;

DETAILED DESCRIPTION OF THE EMBODIMENTS

Embodiments herein describe drug and fluid container systems and a means of implementing those systems. In an embodiment, an automated drug dispenser has multiple chambers. A first chamber is configured to hold a measured amount of water to be taken with a medication. A second chamber is configured to hold multiple chronologically-timed medications. A third chamber is configured to hold fluid and food for meal sustenance.

In another embodiment, an automated drug dispenser has a tablet crusher. A drug chamber contains multiple levels configured to hold chronologically-timed medications, with the next timed medication residing at the second lowest level. The lowest level chamber receives the next timed medication to dispense and crush the tablet medication into a powder. The powder is dispensed with water, which is taken from another chamber of the drug dispenser. Timing circuitry and electronics control the timed dispensing.

In another embodiment, a method of dispensing a timed medication includes holding one or more medications in associated individual levels of a drug chamber. The chambers are configured to be dispensed in chronological order. The method includes receiving a next timed medication into a lower level of the drug chamber, and grinding the medication into a powder. The powder is dispensed with water from another chamber to a patient at a prescribed time. Timing circuitry and electronics control the timed dispensing.

In another embodiment, a multiple-chambered dispenser includes a drug chamber, a water chamber, and a food and fluid chamber. The drug chamber grinds a medication into a powder via blades or rollers and is dispensed with water from the water chamber to a patient. The food and/or fluid chamber provides patient sustenance. The food and/or fluid can be dispensed automatically or manually to the patient.

Figure 1:
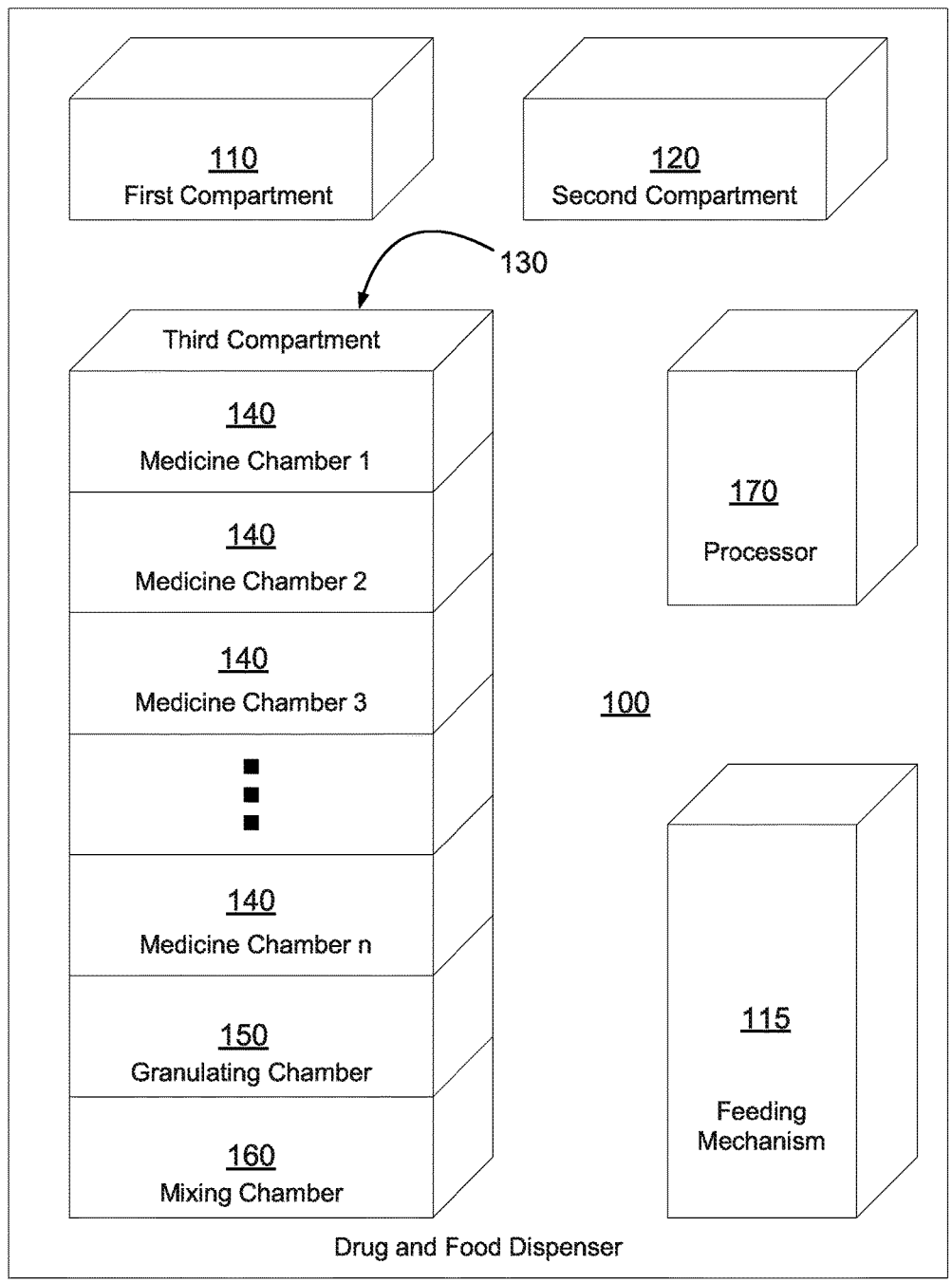
FIG. 1 is a block diagram illustrating a drug and food dispenser according to one embodiment.

FIG. 1 is a block diagram which illustrates certain components of a drug and food dispenser 100 according to embodiments described herein. The components are illustrated as separate units for the sake of simplicity. However, any one of the components can be a separate unit or be physically connected to any other components. A first compartment 110 is a container configured to hold a fluidized food. The fluidized food includes low viscosity foods, such as soup or pureed food or any other food that can be directed from the first compartment 110 through a feeding mechanism 115, such as a feeding tube to be consumed by an individual. The first compartment 110 could include a means for directing the fluidized food to the individual for consumption, such as a pump, which can be manually or electronically controlled. In another embodiment, the drug and food container 100 could be attached to a bed or chair at an elevated position to allow the fluidized food to flow by gravity.

An embodiment of the first compartment 110 includes multiple chambers for multiple types of fluidized food. The first compartment 110 could also be configured to keep one or more chambers of fluidized food at a particular temperature. For example, many foods are ingested at a temperature above room temperature. Therefore, one or more chambers of the first compartment 110 could be insulated or contain a heating element with a controllable heat source. One or more other chambers of the first compartment 110 could be insulated or contain a refrigeration element for keeping the fluidized food of that chamber at a temperature below room temperature. The first compartment 110 could also include an automated message displaying the original date and time of filling the chamber, along with a date and time in which the fluidized food should be discarded.

A second compartment 120 is a container configured to hold a measured amount of fluid, such as water or juice. The measured amount of fluid is configured to be consumed with a medication at a pre-programmed time. The volumes of fluid can also be pre-programmed. For example, a larger amount of fluid may be desired for a larger amount of medication. Also, certain medications may warrant being taken with a large volume of fluid. The second compartment 120 could be connected to a water or fluid source for refilling the second compartment 120 after each medication dispensing. The volume of each successive fluid could be pre-programmed to match the requirements of the next successive medication to be taken.

An embodiment of the second compartment 120 includes multiple chambers for multiple types of fluids. For example, water may be desired to be taken with some medications, while milk may be desired to be taken with other medications. The type of fluid for each chamber can be pre-programmed for the second compartment 120. A further embodiment includes configuring one or more chambers for temperature control of the fluids. For example, it may be desired to keep milk at a temperature below room temperature. One of the chambers could include an insulated chamber or a refrigerated chamber configured to keep the fluid of that chamber at a lower temperature. The second compartment 120 could also include an automated message displaying the original date and time of filling the chamber, along with a date and time in which the fluid should be discarded.

A third compartment 130 includes a plurality of medicine, granulating, and mixing chambers, together configured as a medicine dispenser and granulator. One or more chambers are configured as medicine chambers 140. Each medicine chamber 140 is configured to hold one or more medication pills, which are to be taken at the same time. The medicine chambers 140 are configured, such that the lowest medicine chamber 140 (medicine chamber n) holds the medication pills to be taken next. Each successively higher-positioned medicine chamber 140 holds medication pills to be taken at the next successive designated time. For example, the lowest medicine chamber 140 may contain medication pills to be taken in the morning, a second higher medicine chamber 140 may contain medication pills to be taken at noontime, and a third higher medicine chamber 140 may contain medication pills to be taken in the evening.

The medicine chambers 140 can be configured to be mounted on a stationary rack or a moving rail. The medicine chambers 140 can also be configured to slide up, such that a new medicine chamber 140 could be inserted in between existing medicine chambers 140. For example, three medicine chambers 140 may already be set up, such as the three medicine chambers 140 described above. A new medication may have been recently prescribed, which is to be taken at 10:00 am. Therefore, the new medicine chamber 140 could be inserted in between the lowest medicine chamber 140 and the second lowest medicine chamber 140.

The third compartment 130 also includes a granulating chamber 150, which is configured to grind, chop, or crush the one or more medication pills into a granulated mix or powder. At a pre-programmed time, the medication pills in the lowest medicine chamber 140 would drop into the granulating chamber 150 and be ground, chopped, or crushed into a powder.

For a stationary rack of medicine chambers 140, each medicine chamber 140 could be configured with a processor-controlled opening at a bottom surface for releasing the medication pills into the next lower medicine chamber 140 or into the granulating chamber 150 for the lowest medicine chamber 140. Each medicine chamber 140 could also include a processor-controlled opening at a top surface for receiving medication pills from the next higher-positioned medicine chamber 140. The medicine chambers 140 could be programmed via the processor, such that the lowest medicine chamber 140 initially releases the medication pills contained therein into the granulating chamber 150. Shortly thereafter, the top surface opening of the lowest medicine chamber 140 and the bottom surface opening of the second lowest medicine chamber 140 would open simultaneously via the processor, such that medication pills from the second lowest medicine chamber 140 would drop into the lowest medicine chamber 140. Shortly thereafter, the top surface opening of the second lowest medicine chamber 140 and the bottom surface opening of the third lowest medicine chamber 140 would open simultaneously via the processor, such that medication pills from the third lowest medicine chamber 140 would drop into the second lowest medicine chamber 140. This process would continue for any additional medicine chambers 140 which hold a dosage of medication pills. A moving rail of medicine chambers 140 will be described below with reference to FIGS. 2B-2E.

The third compartment 130 also includes a mixing chamber 160, which is configured to combine and mix the medication powder from the granulating chamber 150 with a measured amount of fluid from the second compartment 120. The combined medication powder and the measured amount of fluid are dispensed through the feeding mechanism 115 to the individual. The third compartment 130 also includes a processor 170, which is configured to execute input instructions pertaining to the processes described herein for the drug and fluid container 100. The processor 170 includes in part, an instruction receiving means, such as a keyboard.

FIG. 2A illustrates an embodiment of a drug and fluid dispenser 200, such as the embodiment described above having a stationary rail. A first compartment 210 is a container configured to hold and forward fluidized food, such as soup or pureed food. The fluidized food can be delivered via a feeding mechanism 215, such as a feeding tube to an individual. A second compartment 220 is a container configured to hold and forward a measured amount of fluid, such as water or juice. The measured amount of fluid is subsequently transported and mixed with a granulated powder of medication, which is delivered to the individual via the feeding mechanism 215. The second compartment 220 can also be configured with an input fluid line configured to refill the second compartment 220 with another measured amount of fluid after each dispensed one or more medicines. A processor 270 contains circuitry that is configured to regulate a valve in conjunction with the input fluid line.

The drug and fluid dispenser 200 also includes one or more medicine chambers 240 (medicine chamber 1 through medicine chamber n). Each of the medicine chambers 240 contains one or more medication pills, which are to be dispensed and taken at the same time by the individual according to a dispensing schedule. The lowest medicine chamber 240 (medicine chamber n) contains the one or more medication pills to be taken at the next scheduled dispensing time. At the prescribed time, the medication pills in the lowest medicine chamber 240 are dropped into a granulating chamber 250, via an opening in the bottom of the lowest medicine chamber 240. The pills are ground, chopped, or crushed into a powdery mixture in the granulating chamber 250. After the pills have been ground, chopped, or crushed, the powdery mixture is dropped into a mixing chamber 260, where the powdery mixture is combined with a measured amount of fluid from the second compartment 220. After the powdery mixture and the measured amount of fluid have been adequately mixed, they are dispensed through the feeding mechanism 215 to the individual. This can be the same feeding mechanism 215 used by the first compartment 210 to dispense fluidized food, wherein a connecting tube 215a from the mixture chamber 260 is joined with the feeding mechanism 215 from the first compartment 210, or it can be a separate feeding mechanism. In an embodiment, a connector 215b could be affixed at a first end to the feeding mechanism 215. The connector 215b could be configured at a second end to be affixed to an endotracheal tube. This would provide a quick connection to the endotracheal tube without requiring removal of the endotracheal tube for feeding and medication purposes.

The mixing chamber 260 can also contain an input line 261 and an output line 262 for rinsing the mixing chamber 260 after each use. Input line 261 is configured to draw fresh water from a water source that partially or completely fills the mixing chamber 260. A valve 261a is located at an end or somewhere within the input line 261 and is configured to regulate, via the processor 270 a measured amount of fluid. The water source could be a direct water connection from a building water source, or it could be a portable fresh water holding tank. The opening of the input line 261 within the mixing chamber 260 can be configured with a pressurized nozzle to aid in cleaning the mixing chamber 260. Waste water from the mixing chamber 260 is removed via a waste water output line 262. The waste water from the mixing chamber 260 could be drained into a building waste water connection, or it could be drained into a portable waste water holding tank via a valve 262a that is located at an end or somewhere within the output line 262 and is controlled by the processor 270.

The processor 270 is configured to execute input instructions pertaining to the processes described herein for the drug and fluid dispenser 200. In the embodiment for a stationary rack of medicine chambers, processor 270 could be located atop the medicine chambers 240. However, processor 270 could be located elsewhere on the drug and fluid dispenser 200 or it could be physically separate from the drug and fluid dispenser 200.

Figure 2B:
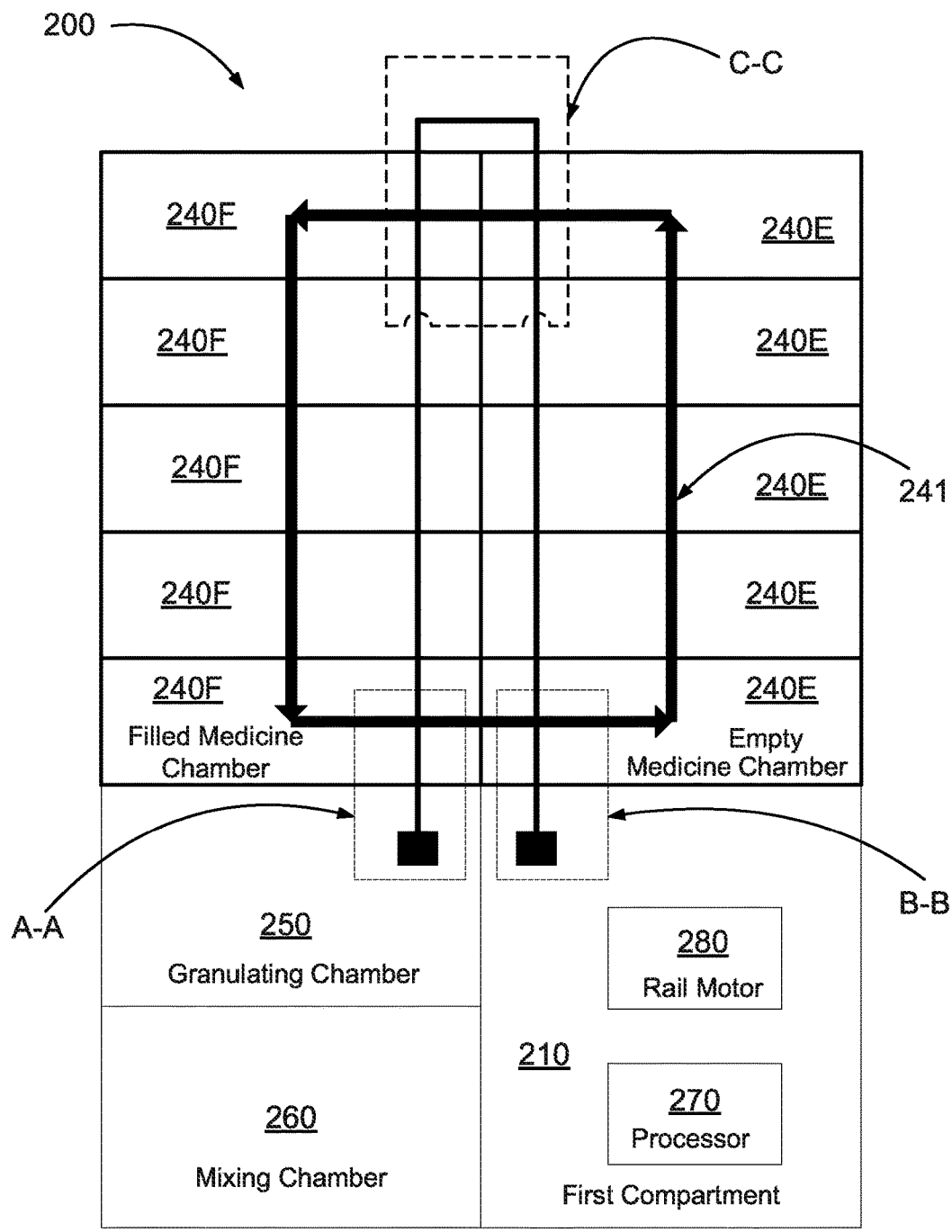

FIGS. 2B-2E illustrate a drug and fluid dispenser using a moving rail, in contrast to the stationary rack of FIG. 2A. The drug and fluid dispenser 200 includes a fluidized food chamber configured to hold and dispense fluidized food to an individual. It also includes a fluid container configured to hold and dispense a measured amount of fluid with a scheduled medication dispensing. The drug and fluid dispenser 200 also includes a plurality of medicine chambers. Each medicine chamber is configured to hold one or more medicines to be taken at a scheduled time. A lower medicine chamber holds one or more medicines to be taken at a first scheduled time, and each subsequently higher-positioned medicine chamber holds one or more medicines to be taken at their respective subsequently scheduled times. The drug and fluid dispenser 200 also includes a mounted rail configured to connect with the plurality of medicine chambers and to forward rotate the plurality of medicine chambers at a next scheduled medication dispensing. A granulating chamber 250 is configured to grind, chop, or crush the one or more medicines into a powder. A mixing chamber 260 is configured to combine and mix the powder with the measured amount of fluid. A feeding mechanism is configured to transport the combined powder and measured amount of fluid from the mixing chamber 260, and is also configured to transport the fluidized food from the fluidized food chamber to the individual. The drug and fluid dispenser 200 also includes a processor 270 having circuitry configured to open one or more doors on a bottom surface of the medicine chamber located directly above the granulating chamber 250, which causes the one or more medicines within the medicine chamber to be released into the granulating chamber 250 at the next scheduled medication dispensing.

FIG. 2B illustrates an embodiment using a moving rail configured to hold and move a plurality of medicine chambers. FIG. 2B is a side view of a drug and fluid dispenser 200, similar to the drug and fluid dispenser 200 in FIG. 2A. A first compartment 210 containing fluidized food is located on the bottom right side of the view. A granulating chamber 250 is located on the bottom left side atop a mixing chamber 260 in FIG. 2B. The mixing chamber 260 can also include a clean water input line configured to rinse the mixing chamber 260 after each dispensed one or more medicines, and a waste water output line configured to remove contents of the rinsed mixing chamber 260 as shown in FIG. 2A.

The first compartment 210, the granulating chamber 250, and the mixing chamber 260 remain stationary during the dispensing process. A processor 270 is located on the side of the first compartment 210, such that it also remains stationary. A rail motor 280 is also located on the side of the first compartment 210, which is configured to drive the moving medicine chambers 240. The rail motor 280 could be electrically powered or it could be powered by a portable rechargeable battery. Either processor 270 or rail motor 280 could be located elsewhere on the drug and fluid dispenser 200, or either one could be located physically separate from the drug and fluid dispenser 200. In either case, both processor 270 and rail motor 280 need to be located apart from the moving medicine chambers 240E and 240F.

The top left side of FIG. 2B illustrates a plurality of filled medicine chambers 240F. The filled medicine chambers 240F are arranged chronologically, wherein the next medication to be dispensed is located in the lowest filled medicine chamber 240F, directly above the granulating chamber 250. Each successively higher filled medicine chamber 240F above the lowest filled medicine chamber 240F is programmed to be dispensed in a respective successive order. The top right side of FIG. 2B illustrates a plurality of empty medicine chambers 240E.

FIG. 2B also illustrates a rail 241 that is configured to move the medicine chambers 240F and 240E in a circular pattern. The rail 241 contains protrusions or latches at various positions, which are configured to connect with a receptor on the front surface of each medicine chamber 240F and 240E. The protrusions fit into the medicine chamber receptors, such that the medicine chambers 240F and 240E are moved in the same circular pattern as the rail 241. The rail 241 is powered or driven by rail motor 280. The lowest filled medicine chamber 240F dumps its contents into the granulating chamber 250 at its respective scheduled dispensing. After the contents have been dumped, the rail 241 moves the medicine chamber (now empty) horizontally across to the top surface of the first compartment 210. This process is repeated at the next scheduled medication dispensing. This results in filled medicine chambers 240F moving towards the granulating chamber 250, while moving the empty medicine chambers 240E away from the granulating chamber 250.

FIG. 2C illustrates a side view of FIG. 2B, in which the rail 241 contains multiple protrusions 242, each of which fit into a receptacle 243 of a respective medicine chamber 240F or 240E. In FIG. 2C, the rail and the connected medicine chambers 240 are moving downward.

FIG. 2D illustrates a detailed view of the front of a medicine chamber 240F or 240E. The receptacle 243 is located near the center front face of each medicine chamber 240F or 240E, wherein a respective protrusion 242 from the rail 241 fits into each receptacle 243. Medicine chambers 240F and 240E can also include a beveled surface 244 along two or more inside walls of the medicine chamber 240F or 240E. The beveled surfaces 244 aid in keeping the medication pills together at the center of the bottom surface of the medicine chamber 240F or 240E, where an opening is located. The opening can include one or two doors 245, which open at a programmed time according to a medication dispensing schedule. When the doors open, the medication pills will drop into the granulating chamber 250.

FIG. 2E illustrates a side view of the area designated as A-A in FIG. 2B, in which the lowest filled medicine chamber 240F is located directly above the granulating chamber 250. The rail will stop moving when a filled medicine chamber 240F is located directly above the granulating chamber 250. After the doors 245 have opened to drop the medication pills into the granulating chamber 250, the rail will begin to move again. A rail mount 246 is illustrated in which a base of the rail mount 246 is affixed to the side of the granulating chamber 250. The rail mount 246 contains a rail guide 247 through which the rail 241 moves. The rail guide 247 mounted to the rail mount 246 are both stationary, while the rail 241 moves through the rail guide 247. In FIG. 2E, the rail 241 is moving into the page. In FIG. 2B, the rail 241 is moving from the left side of the page atop the granulating chamber 250 towards the right side of the page atop the first compartment 210.

A similar arrangement as illustrated in FIG. 2E can be configured for a side view of B-B illustrated in FIG. 2B, in which the rail mount 246 is affixed to the side of the first compartment 210. Another similar arrangement can be configured for a side view of C-C illustrated in FIG. 2B, in which the rail mount 246 is not affixed to another structure, but the top ends of the rail mount 246 can be connected together for additional stability. All other features for side views of B-B and C-C are similar to the side view of A-A, discussed with reference to FIG. 2E.

The rail 241 will remain stationary, except to move the lowest filled medicine chamber 240F into place over the granulating chamber 250 when the next dispensing of medication is scheduled. This will also move the last emptied medicine chamber 240E from atop the granulating chamber 250 to a position directly atop the first compartment 210. While the rail 241 is stationary, one or more of the empty medicine chambers 240E can be refilled with a scheduled medication dispensing, which would follow the last filled medicine chamber 240F. In addition, some or all of the empty medicine chambers 240E can be filled with future successive medications in their respective scheduled slots. As soon as medication pills from the lowest filled medicine chamber 240F have been emptied into the granulating chamber 250 and the now-empty medicine chamber 240E has moved atop the first compartment 210, it can be filled again with the next prescribed medication. In another embodiment, the next scheduled filled medicine chamber 240F can move into place over the granulating chamber 250 as soon as the previous medicine chamber 240 has emptied its contents and moved atop the first compartment 210. In still another embodiment, the emptied medicine chambers 240E can be dropped into a receptacle instead of remaining attached to the rail 241.

Figure 3A:
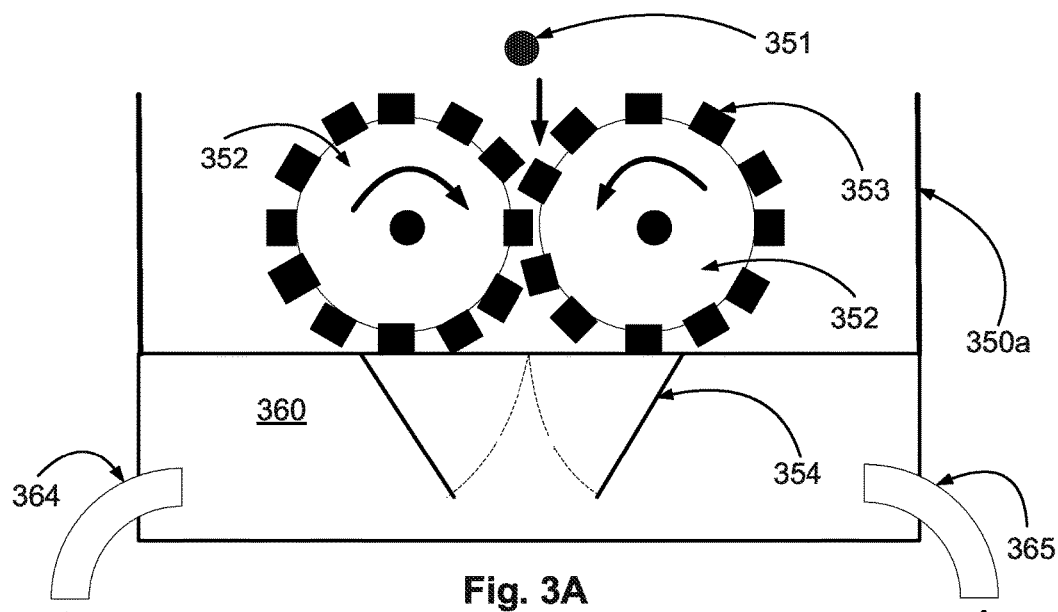
FIG. 3A is a block diagram illustrating a granulating chamber having crushing rollers according to one embodiment.

The granulating chamber 250 can be configured to grind, chop, or crush the medication pills into a powder that are emptied from a medicine chamber. Any other method and associated device that breaks up the medication pills into fine particles is contemplated by embodiments described herein. FIG. 3A illustrates a granulating chamber 350a (as a specific embodiment of the above-described granulating chamber 250) that is configured to crush medication pills 351 which are dispensed from a medicine chamber located atop the granulating chamber 350a. The granulating chamber 350a can be used with the drug and fluid containers described with reference to FIGS. 1 and 2A, as well as the drug and fluid containers described with reference to FIGS. 2B-2E. One medication pill 351 is illustrated in FIG. 3A for the sake of simplicity. However, multiple medication pills 351 can be dispensed simultaneously. In another embodiment, multiple medication pills 351 can be successively dropped after a designated period of time between each dropped medication pill 351 has elapsed.

Two rollers 352 are illustrated in FIG. 3A, which rotate inwardly towards each other in opposite directions. In an alternative embodiment, the granulating chamber 350a could have just one roller 352, which is configured to crush the medication pills against a fixed surface, such as a floor, wall, or corner of the granulating chamber 350. Each roller 352 has a plurality of protrusions or teeth 353. Each tooth 353 on a roller 352 is spaced such that a tooth of the left roller 352 will fit in between two teeth 353 of the right roller 352, and vice versa. A roller motor can be located on the exterior surface of the granulating chamber 350a, which is configured to drive the rollers 352. The rollers 352 can be programmed to rotate for a designated period of time, depending upon the size and number of medication pills within the medicine chamber. Variable settings of short, medium, or long periods of time can be designated, or an actual time can be entered. In addition, the velocity of rotation of the rollers 352 can be varied, such as slow, medium, or fast, or an actual velocity can be entered.

After the designated crushing time has expired, the resultant medication powder sits atop an opening in the bottom surface of the granulating chamber 350a. One or two doors 354 will open to drop the medication powder into the mixture chamber 360 (as a specific embodiment of the mixing chamber 160 described above), which resides below the granulating chamber 350a. The medication powder in the mixing chamber 360 will be mixed with a measured amount of fluid from the second compartment, via an input line 364. When the medication powder and measured amount of fluid have been mixed after a pre-determined amount of time, the mixture is dispensed via an output line 365 to a feeding mechanism, such as feeding mechanism 215 of FIG. 2A.

Figure 3B:
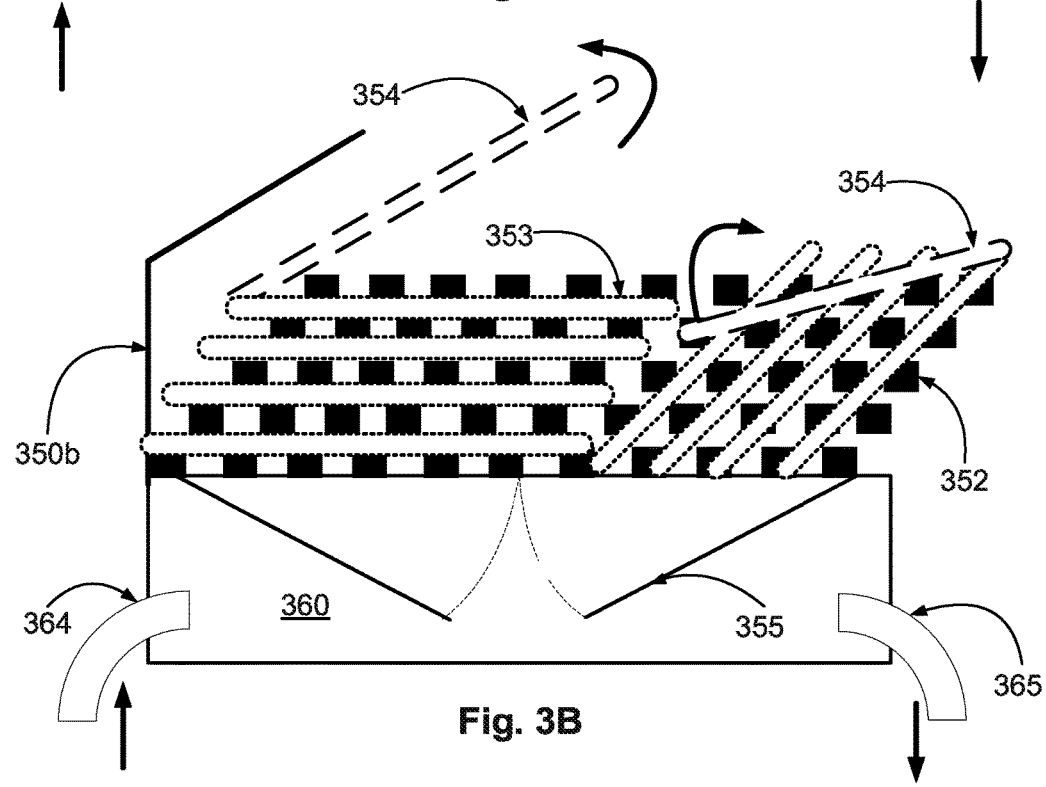
FIG. 3B is a block diagram illustrating a granulating chamber having chopping blades according to one embodiment.

FIG. 3B illustrates a further embodiment of a granulating chamber 350b configured to chop one or more medication pills that are dispensed from a medicine chamber positioned directly over the granulating chamber 350b. The granulating chamber 350b can be used with the drug and fluid containers described with reference to FIGS. 1 and 2A, as well as the drug and fluid containers described with reference to FIGS. 2B-2E. The bottom surface of the granulating chamber 350b contains a matrix of raised fixtures 352 with gaps 353 in between the raised fixtures 352. FIG. 3B illustrates rectangular raised fixtures 352. However, other geometric shapes of raised fixtures 352 are contemplated by embodiments described herein, including but not limited to a round, oval, triangle, pentagon, hexagon, or octagon raised fixtures. A screen could reside at the bottom surface of the gaps 353 to collect the chopped pieces of medication pills.

One or more blades 354 attached to an inside wall of the granulating chamber 350b are configured to rotate up and down and to fit within the gaps 353 between the raised fixtures 352, such that any medication pills located within a gap 353 will be chopped when the blade 354 is lowered. One set of blades 354 can be positioned in a fully extending side-to-side arrangement between the raised fixtures 352. Alternatively, two sets of opposing blades 354 could be positioned halfway in a side-to-side arrangement between the raised fixtures 352. In addition, one fully-extending set or two opposing sets of blades 354 in a front-to-back configuration could be positioned between the raised fixtures 352. The side-to-side configuration of blades 354 could operate in alternating fashion with the front-to-back configuration of blades 354.

When a pre-determined period of time for chopping has elapsed, doors 355 located on the bottom surface of the granulating chamber 350b will open to drop the resultant medication powder down into the mixing chamber 360. A measured amount of fluid from the second chamber will fill into the mixture chamber 360 from input line 364 to be mixed with the powdered medication. When a pre-determined period of time for mixing has elapsed, the mixture of powdered medication and fluid will be dispensed via output line 365 to a feeding mechanism, such as feeding mechanism 215 of FIG. 2A.

Figure 3C:
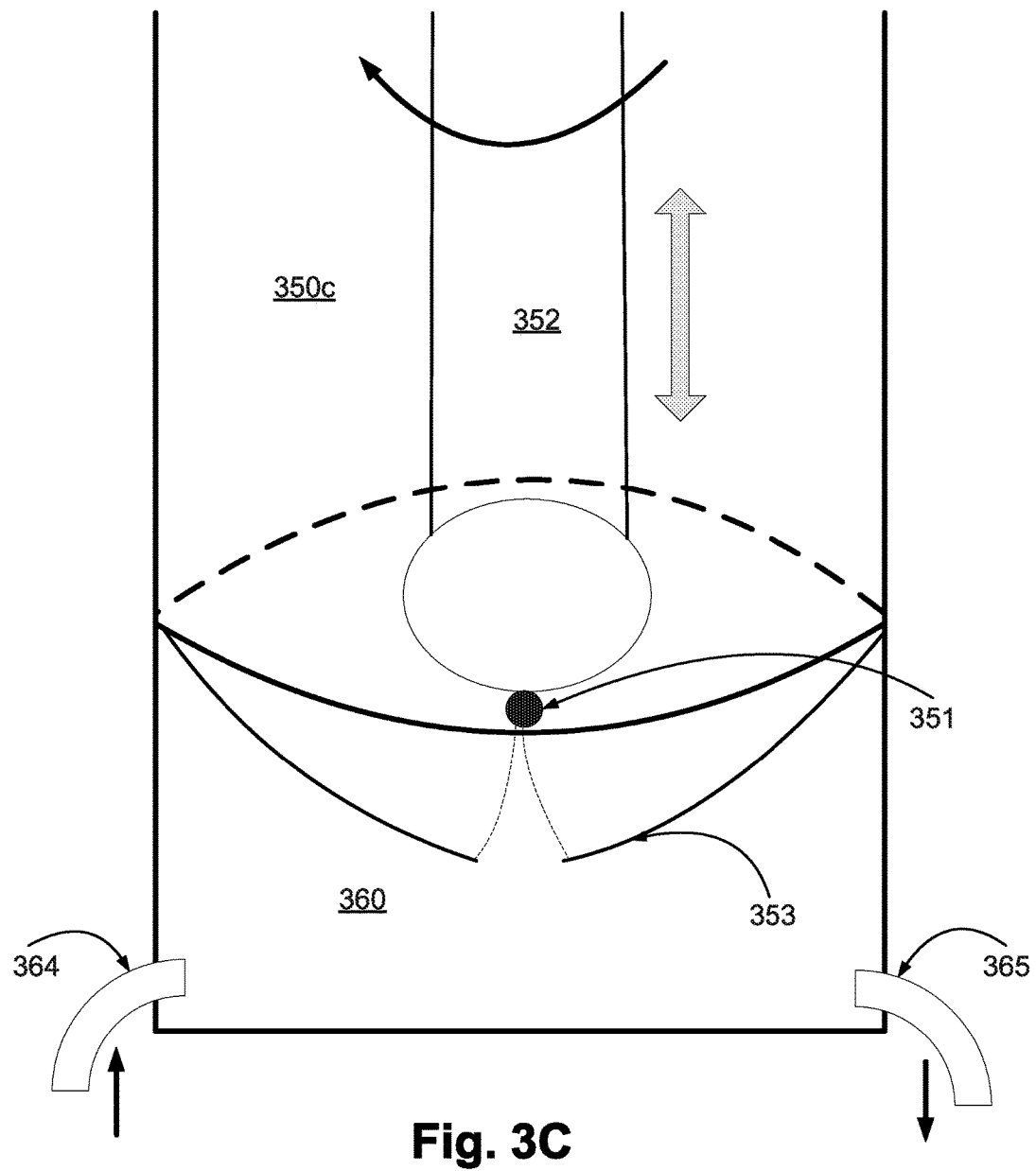
FIG. 3C is a block diagram illustrating a granulating chamber having a grinding pedestal according to one embodiment.

FIG. 3C illustrates a further embodiment of a granulating chamber 350c configured to grind one or more medication pills 351 that are dispensed from a medicine chamber positioned directly over the granulating chamber 350c. The granulating chamber 350c can be used with the drug and fluid containers described with reference to FIGS. 1 and 2A, as well as the drug and fluid containers described with reference to FIGS. 2B-2E. A pedestal 352 is configured to exert force onto the medication pills 351, which are pressed against a concave bottom surface of the granulating chamber 350c. The pedestal 352 is also configured to rotate and/or move up and down while exerting force against the medication pills 351. When a pre-determined amount of time has elapsed, doors 353 will open to release the resultant powdery medication into the mixture chamber 360. The powdery medication mixture will be combined with a measured amount of fluid from the second compartment via input line 364. When a pre-determined period of time for mixing has elapsed, the mixture of powdered medication and fluid will be dispensed via output line 365 to a feeding mechanism, such as feeding mechanism 215 of FIG. 2A.

Figure 4:
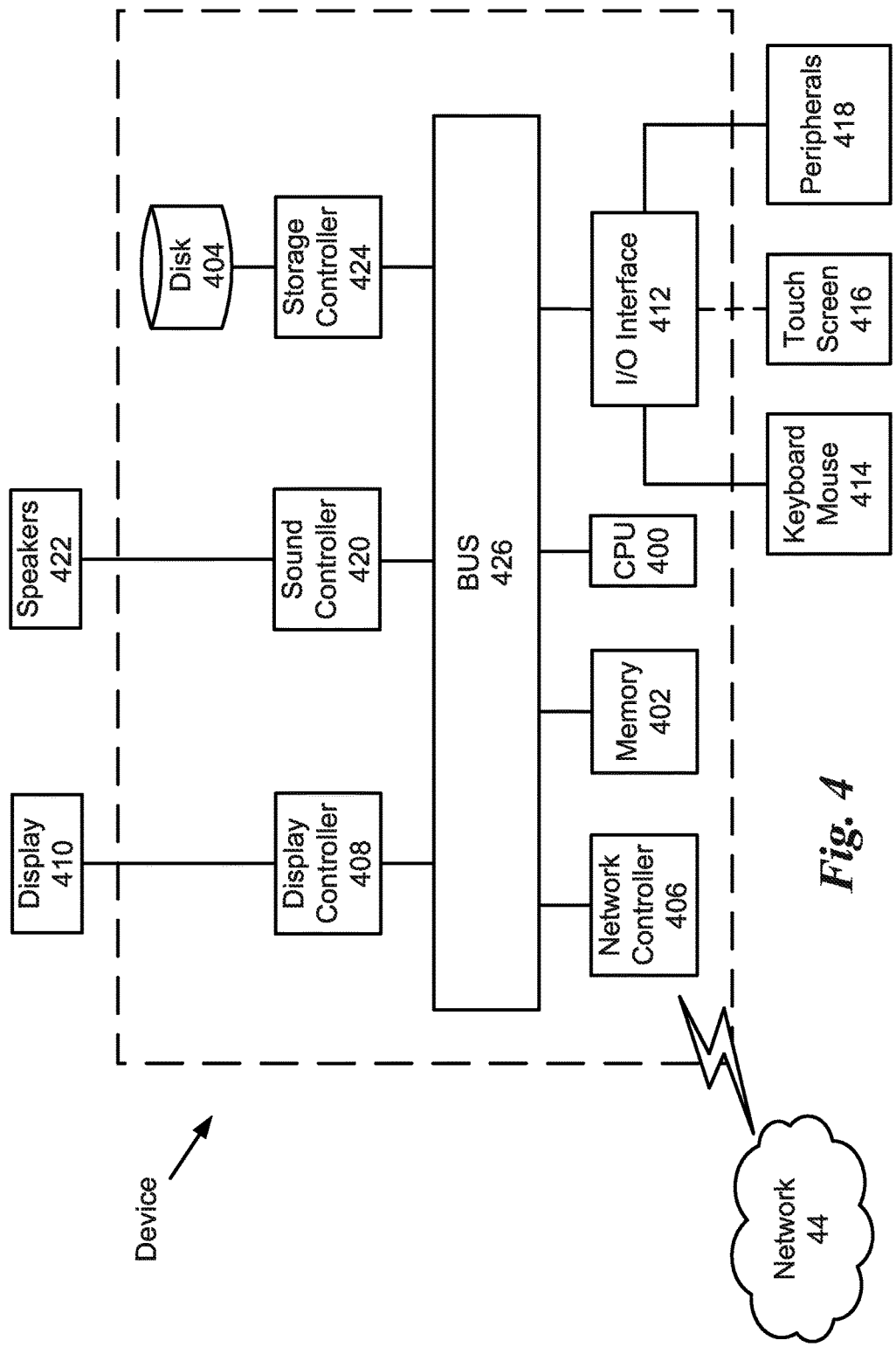
FIG. 4 is a block diagram of an exemplary computing device according to embodiments described herein.

A hardware description is given with reference to FIG. 4 for a computing device, such as the processors 170 and 270, as well as databases and/or servers used in conjunction with associated circuitry for embodiments described herein. In FIG. 4, the computing device includes a CPU 400 which performs the processes described above. The process data and instructions may be stored in memory 402. These processes and instructions may also be stored on a storage medium disk 404 such as a hard disc drive (HDD) or portable storage medium or may be stored remotely. Further, the claimed embodiments are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claimed embodiments may be provided as a utility application, background daemon, or component of an operating system, or combination thereof, executing in conjunction with CPU 400 and an operating system such as Microsoft Windows 7, UNIX, Solaris, LINUX, Apple MAC-OS and other systems known to those skilled in the art.

CPU 400 may be a Xenon or Core processor from Intel of America or an Opteron processor from AMD of America, or may be other processor types that would be recognized by one of ordinary skill in the art. Alternatively, the CPU 400 may be implemented on an FPGA, ASIC, PLD or using discrete logic circuits, as one of ordinary skill in the art would recognize. Further, CPU 400 may be implemented as multiple processors cooperatively working in parallel to perform the instructions of the inventive processes described above.

The computing device in FIG. 4 also includes a network controller 406, such as an Intel Ethernet PRO network interface card from Intel Corporation of America, for interfacing with network 44. As can be appreciated, the network 44 can be a public network, such as the Internet, or a private network such as an LAN or WAN network, or any combination thereof and can also include PSTN or ISDN sub-networks. The network 44 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 408, such as a NVIDIA GeForce GTX or Quadro graphics adaptor from NVIDIA Corporation of America for interfacing with display 410, such as a Hewlett Packard HPL2445w LCD monitor. A general purpose I/O interface 412 interfaces with a keyboard and/or mouse 414 as well as a touch screen panel 416 on or separate from display 410. General purpose I/O interface 412 also connects to a variety of peripherals 418 including printers and scanners, such as an OfficeJet or DeskJet from Hewlett Packard.

A sound controller 420 is also provided in the computing device, such as Sound Blaster X-Fi Titanium from Creative, to interface with speakers/microphone 422 thereby providing sounds and/or music. The general purpose storage controller 424 connects the storage medium disk 404 with communication bus 426, which may be an ISA, EISA, VESA, PCI, or similar, for interconnecting all of the components of the computing device. A description of the general features and functionality of the display 410, keyboard and/or mouse 414, as well as the display controller 408, storage controller 424, network controller 406, sound controller 420, and general purpose I/O interface 412 is omitted herein for brevity as these features are known.

The computing devices used with embodiments described herein may not include all features described in FIG. 4. In addition, other features used with embodiments described herein may not be described with reference to FIG. 4.

Embodiments described herein can be used in conjunction with other systems, devices, and structures. In one embodiment, any of the drug and fluid containers described herein could be attached to or set up near a patient's bed or chair for feeding and medication dispensing. This would be advantageous in a hospital setting or an extended home health care environment by freeing up medical assistants for other tasks and also ensuring all medications are dispensed at their scheduled times. In addition, a nursing home facility would benefit from the drug and fluid containers described herein, since many nursing home patients have difficulty in swallowing food and pills and in some cases, are incoherent or uncooperative.

The foregoing discussion discloses and describes merely exemplary embodiments of drug and fluid containers. As will be understood by those skilled in the art, the drug and fluid containers may be embodied in other specific forms without departing from the spirit or essential characteristics thereof. Accordingly, the disclosure herein is intended to be illustrative, but not limiting of the scope of the embodiments, as well as other claims. The disclosure, including any readily discernible variants of the teachings herein, define in part, the scope of the foregoing claim terminology such that no inventive subject matter is dedicated to the public.

The invention claimed is:

1. A drug and fluid dispenser, comprising:
   a fluidized food chamber configured to hold and dispense fluidized food to an individual;
   a fluid container configured to hold and dispense a measured amount of fluid with a scheduled medication dispensing;
   a plurality of medicine chambers, each medicine chamber configured to hold one or more medicines to be taken at a scheduled time, wherein a lower medicine chamber holds one or more medicines to be taken at a first scheduled time, and each subsequently higher-positioned medicine chamber holds one or more medicines to be taken at their respective subsequently scheduled times;
   a mounted rail configured to connect with the plurality of medicine chambers and to forward rotate the plurality of medicine chambers at a next scheduled medication dispensing;
   a granulating chamber configured to grind, chop, or crush the one or more medicines from one of the medicine chambers into a powder;
   a mixing chamber configured to combine and mix the powder with the measured amount of fluid;
   a feeding mechanism configured to transport the combined powder and measured amount of fluid from the mixing chamber and to transport the fluidized food from the fluidized food chamber to the individual; and
   a processor circuit configured to open one or more doors on a bottom surface of the medicine chamber located directly above the granulating chamber, thereby releasing the one or more medicines within the medicine chamber into the granulating chamber at the next scheduled medication dispensing.

2. The drug and fluid dispenser of claim 1, wherein the plurality of medicine chambers include filled medicine chambers and empty medicine chambers.

3. The drug and fluid dispenser of claim 2, wherein the mounted rail is configured to rotate filled medicine chambers towards the granulating chamber and rotate empty medicine chambers away from the granulating chamber under control of the processor circuit.

4. The drug and fluid dispenser of claim 1, wherein the granulating chamber includes one or more crushing rollers.

5. The drug and fluid dispenser of claim 1, wherein the granulating chamber includes a plurality of chopping blades.

6. The drug and fluid dispenser of claim 1, wherein the granulating chamber includes a downwardly projecting rounded head configured to grind the one or more medicines against a concave bottom surface of the granulating chamber.

7. The drug and fluid dispenser of claim 1, further comprising:
- a clean water input line configured to rinse the mixing chamber after each dispensed one or more medicines; and
- a waste water output line configured to remove contents of the rinsed mixing chamber.

* * * * *